(12) United States Patent
Mallavarapu et al.

(10) Patent No.: US 9,103,797 B2
(45) Date of Patent: Aug. 11, 2015

(54) ANIONIC SURFACTANT DETECTION

(71) Applicant: CRC CARE Pty, Ltd., Mawson Lakes (AU)

(72) Inventors: Megharaj Mallavarapu, Panorama (AU); Ravendra Naidu, Pasadena (AU); Philip Mercurio, Felixstow (AU)

(73) Assignee: CRC CARE Pty Ltd, Mawson Lakes (AU)

( * ) Notice: Subject to any disclaimer, the term of this patent is extended or adjusted under 35 U.S.C. 154(b) by 0 days.

(21) Appl. No.: 13/622,425

(22) Filed: Sep. 19, 2012

(65) Prior Publication Data
US 2013/0017619 A1    Jan. 17, 2013

Related U.S. Application Data

(63) Continuation of application No. 12/756,753, filed on Apr. 8, 2010, now abandoned.

(30) Foreign Application Priority Data

Oct. 8, 2008 (WO) ................ PCT/AU2008/001494

(51) Int. Cl.
*G01N 21/00* (2006.01)
*G01N 21/78* (2006.01)
(52) U.S. Cl.
CPC ..................................... *G01N 21/78* (2013.01)
(58) Field of Classification Search
None
See application file for complete search history.

(56) References Cited

FOREIGN PATENT DOCUMENTS

| | | |
|---|---|---|
| EP | 0 611 966 | 8/1994 |
| JP | 2000 241407 | 9/2000 |
| WO | AU2008/001494 | 12/2008 |

OTHER PUBLICATIONS

Motomizu et al., "Flow-injection method for the determination of anionic surfactants after liquid-liquid extraction using on-tube visible absorption and fluoresence detection" *Analytic Chimaca Acta*, 1992, vol. 261(1-2), pp. 471-475.
Patel et al., "Flow injection determination of anionic surfactants with cationic dyes in water bodies of central India" *Analyst*, 1998, vol. 123(8), pp. 1691-1695.
Fytianos et al., "Spectrophotometric determination of Anionic Surfactants in Aqueous and Environmental Water Samples with Cationic Dyes" *Journal of Enfiromental Science and Cotnrol*, 1997, vol. A32(4), pp. 953-962.
Motomizu et al., Sovent Extration-Spectrophotometric Determination of Anionic Surfactants with Ethyl Violet, 1982, Analytical Chemistry, vol. 54(3), pp. 392-397.
Lukaszewski, Z., "Resolved and unresolved questions of analysis of surfactants in the aquatic environment", 1998. Studies in Surface Science and Catalysis, vol. 120, pp. 135-176.
Schmitt, TM, "Analysis of surfactants", 2001, Environmental Analysis, p. 547.
Supplemental European Search Report in EP Application No. EP 08 80 0129. dated Apr. 29, 2014.

*Primary Examiner* — Robert Xu
(74) *Attorney, Agent, or Firm* — Dunlap Codding, P.C.

(57) ABSTRACT

Disclosed herein are methods for the detection and/or quantification of anionic surfactants. Also disclosed herein are test kits, which utilize the disclosed methods, to estimate the anionic surfactant concentration in samples, such as environmentally-derived samples. In some specific embodiments, the method and the test kit may be used to detect, among other things, aqueous film forming foams that comprise anionic surfactants.

16 Claims, 6 Drawing Sheets

A

B

A

B

A

B

C

D

ANIONIC SURFACTANT DETECTION

TECHNICAL FIELD OF THE INVENTION

Disclosed herein are methods for the detection and/or quantification of anionic surfactants. Also disclosed herein are test kits, which utilize the disclosed methods, to estimate the anionic surfactant concentration in samples, such as environmentally-derived samples. In some specific embodiments, the method and the test kit may be used to detect, among other things, aqueous film forming foams that comprise anionic surfactants.

BACKGROUND OF THE INVENTION

Surfactants are a group of organic compounds that are of increasing concern. They are a group of chemicals that are in widespread use around the world with global production exceeding $9.86 \times 10^9$ kg per year. Surfactants are used in large amounts daily in households around the world in cleaning products and detergents, in industrial applications including the manufacturing of pesticides, plasticizers in the cement and concrete industries, mining, pharmaceuticals and many other products.

Anionic surfactants are the major class of surfactants that are used in detergents. Linear alkylbenzene sulfonate (LAS) is published to be the most widely used anionic surfactant. Wastewater treatment facilities receive anionic surfactants in significant amounts due to the enormous use of detergents for washing purposes and from other sources. While most of the surfactants are able to be eliminated through conventional wastewater treatment, some surfactants have low biodegradability and, in others, undesired biodegradation products are formed and discharged with effluents into surface waters. Another route for introducing these chemicals into the environment includes the use of sewage sludge as fertilizer in agriculture. The surfactants can leach into the surrounding soils and be further transported to groundwater and surface waters.

One particular class of specialty surfactants, fluorinated surfactants, have properties that make them particularly well suited to fire-fighting applications. PFOS (perfluorooctane sulfonate C8F17SO3) and PFOA (perfluorooctanoic acid C7F15CO2H) are two commonly used fluorinated surfactants. These surfactants have been detected in human blood, water, soils, sediments, air, and biota samples. The compounds have been found to be globally distributed, persistent and bioaccumulative.

In order to be able to detect anionic surfactant contamination in the environment, various assays for the detection of anionic surfactants have been developed.

The Methylene Blue Active Substances (MBAS) assay is the current standard colorimetric test used to estimate the concentration of anionic surfactants in water. The water sample is acidified, 3 mL of chloroform and a methylene blue solution is added, then the sample is agitated. In the MBAS assay, the anionic surfactant complexes with the cationic dye. The higher the concentration of anionic surfactant, the more the dye is absorbed and the greater the colorimetric change. For method sensitivity, LAS is used to estimate the concentration of anionic surfactant, and concentrations are reported in LAS equivalents. The MBAS assay has a published detection limit of 0.025 mg/L.

While this method has been used extensively, the use of the assay is problematic since it uses chloroform as the extraction solvent, which is a suspected human carcinogen. Thus, a need exists for an improved assay for the detection of anionic surfactants. It would be desirable that such an assay would eliminate the use of the suspected carcinogenic solvent, chloroform. It would also be desirable if an improved assay was suitable for use in the field for the rapid detection of anionic surfactants in environmental samples.

Reference to any prior art in this specification is not, and should not be taken as, an acknowledgment or any form of suggestion that this prior art forms part of the common general knowledge in any country.

SUMMARY OF THE INVENTION

Figure 1:
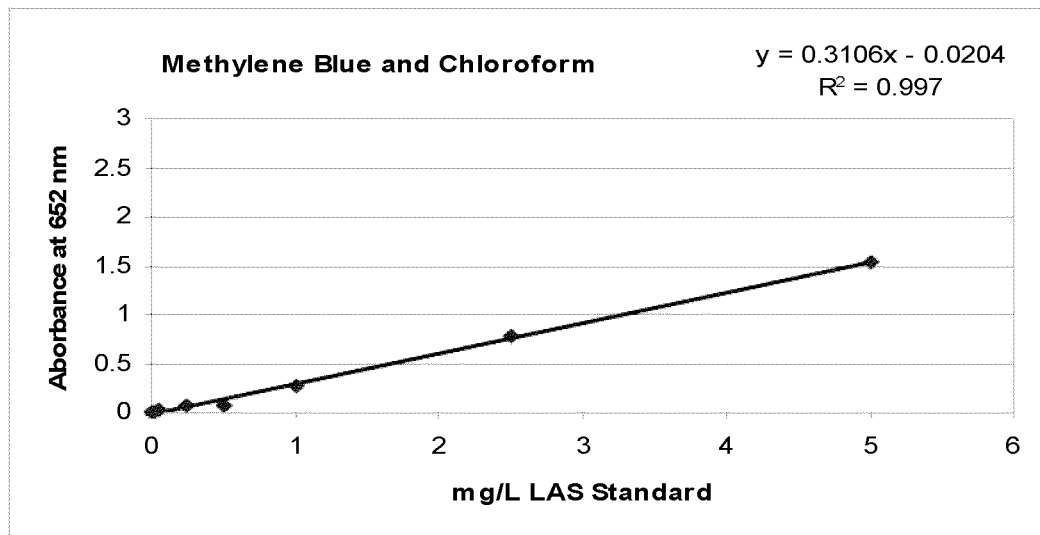
FIG. 1 shows a comparison of the MBAS assay with the EVEA-AS assay using LAS as a calibration standard. Panel A shows absorbance in the solvent phase after using the MBAS assay with varying concentrations of LAS in a sample. Panel B shows absorbance in the solvent phase after using the EVEA-AS assay with varying concentrations of LAS in a sample.
Figure 1:
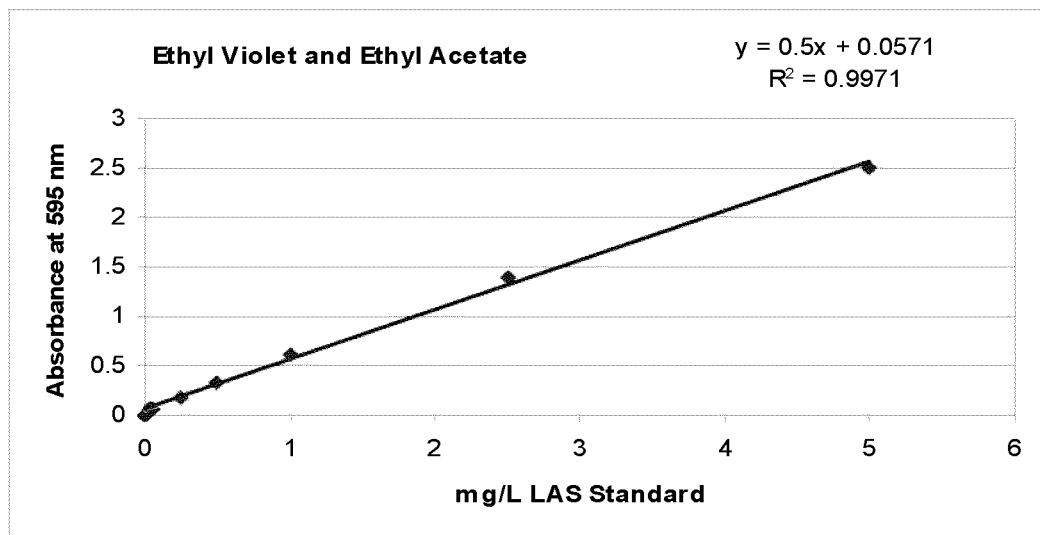

The present invention is predicated, in part, on a method and kit for the detection and/or quantification of anionic surfactants.

In a first aspect, the present invention provides a method for detecting and/or quantifying an anionic surfactant in a sample, the method comprising:

providing a cationic dye, wherein the cationic dye is capable of complexing with an anionic surfactant from the sample to form a detectable dye-surfactant complex that is preferentially soluble in a solvent which is substantially immiscible with the sample;

providing a solvent which is substantially immiscible with the sample;

contacting the cationic dye with either the sample and the solvent or an extract of the sample in the solvent such that an anionic surfactant in the sample or extract complexes with the cationic dye to form a detectable dye-surfactant complex that is preferentially soluble in the solvent;

detecting and/or quantifying the dye-surfactant complex in the solvent, wherein the presence of the dye-surfactant complex in the solvent indicates the presence of an anionic surfactant in the sample.

In one embodiment the cationic dye comprises ethyl violet or a derivative thereof.

In a further embodiment, the solvent comprises ethyl acetate.

In at least some embodiments, the disclosed method has been identified to provide increased sensitivity and resolution for the detection and/or quantification of anionic surfactants over standard anionic surfactant detection methods such as the methylene blue active substances (MBAS) assay.

Furthermore, at least some embodiments of the disclosed method are particularly suitable for a field-based assay for anionic surfactants.

In a second aspect, the present invention provides a kit for detecting and/or quantifying an anionic surfactant in a sample, the kit comprising:

a cationic dye, wherein the cationic dye is capable of complexing with an anionic surfactant from the sample to form a detectable dye-surfactant complex that is preferentially soluble in a solvent which is substantially immiscible with the sample; and instructions for performing the method according to the first aspect of the invention.

The method and kit disclosed herein may be used for detecting any suitable anionic surfactant. However, in some specific embodiments, the method and kit are suitable for detecting an anionic surfactant constituent of an aqueous film forming foam and/or a fluorinated anionic surfactant.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

TABLE 1

Summary of abbreviations used in the specification

| Abbreviation | Meaning |
| --- | --- |
| AFFF | aqueous film forming foam |
| EVEA-AS | ethyl violet ethyl acetate active substances |
| LAS | linear alkylbenzene sulfonate |
| MBAS | methylene blue active substances |
| PFOA | perfluorooctanoic acid |
| PFOS | perfluorooctane sulfonate |
| SDS | sodium dodecyl sulfate |
| SPE | solid phase extraction |

DETAILED DESCRIPTION OF THE INVENTION

It is to be understood that the following description is for the purpose of describing particular embodiments only and is not intended to be limiting with respect to the above description.

In a first aspect, the present invention provides a method for detecting and/or quantifying an anionic surfactant in a sample, the method comprising:

providing a cationic dye, wherein the cationic dye is capable of complexing with an anionic surfactant from the sample to form a detectable dye-surfactant complex that is preferentially soluble in a solvent which is substantially immiscible with the sample;

providing a solvent which is substantially immiscible with the sample;

contacting the cationic dye with either the sample and the solvent or an extract of the sample in the solvent such that an anionic surfactant in the sample or extract complexes with the cationic dye to form a detectable dye-surfactant complex that is preferentially soluble in the solvent;

detecting and/or quantifying the dye-surfactant complex in the solvent, wherein the presence of the dye-surfactant complex in the solvent indicates the presence of an anionic surfactant in the sample.

As set out above, the methods disclosed herein are for the detection of an anionic surfactant in a sample. As would be readily understood by a person skilled in the art, a "surfactant" is an amphipathic molecule comprising both a hydrophobic portion and hydrophilic portion. In the case of an "anionic surfactant", the hydrophilic portion of the molecule generally carries a negative charge at least at a pH of 7 or greater. As such, the term "anionic surfactant" may include molecules such as carboxylic acids which may form an anion (ie. a conjugate base) at a pH of 7 or greater, but which may not necessarily be in an anionic form at a pH lower than 7. For example a carboxylic acid surfactant in an environmental sample may be regarded as an anionic surfactant even if the carboxylic acid surfactant is not necessarily in an anionic form until it is in the presence of a base such as a basic cationic dye.

A range of anionic surfactants that may be detected and/or quantified using the disclosed method would be readily ascertained by a person skilled in the art. Exemplary anionic surfactants include, for example, linear alkylbenzene sulfonate (LAS), sodium dodecyl sulfate (SDS), fluorinated surfactants such as perfluorooctane sulfonate (PFOS) or perfluorooctanioic acid (PFOA), and the like.

The method also has particular application for the detection and/or quantification of anionic surfactants which are constituents of aqueous film forming foams (AFFF), such as the fluorinated surfactants mentioned above. Exemplary AFFFs include Light Water™ (3M, St. Paul, Minn., USA) and Ansulite (Ansul Incorporated, Marinette, Wis., USA).

As also set out above, the method contemplates the detection and/or quantification of an anionic surfactant in a sample.

In one embodiment, the "sample" may be an aqueous or water-based sample. In some embodiments, the aqueous sample may be an environmentally derived sample such as a water sample, a soil dilution or the like. The sample may be derived from, for example, industrial sites, sites suspected of surfactant contamination, such as sites where AFFFs have been used, industrial or domestic effluents, treated water samples, stormwater samples, lake or river water or sediment samples, marine water or sediment samples, among many others.

As would be appreciated, aqueous samples may also be derived from solids. For example, soils may be diluted in water or another aqueous solvent to produce a sample. Furthermore, other solids such as plant material, building material or the like may be crushed or macerated before being diluted into water or another aqueous solvent to produce a sample.

In further embodiments, samples may be extracted into the solvent used in the assay. In these embodiments, the solvent may be added to the sample which may be solid, semi-solid or liquid. Examples of such samples may include soils, plant material, building material or the like.

In one embodiment, the solvent and dye may both be added to the sample and any anionic surfactant in the sample complexes with the cationic dye to form a detectable dye-surfactant complex that is preferentially soluble in the solvent. In a further embodiment, where the anionic surfactant and dye are soluble in the solvent used, the anionic surfactant and dye may dissolve into the solvent and the complex between the anionic surfactant and dye may form within the solvent phase. In a further embodiment, the solvent may be added to the sample to form an extract of the sample in the solvent for use in the assay. In some embodiments, the sample may be separated from the extract, or they may be used as a mixture. In any event, the cationic dye may be added to such extracts in order to allow the formation of a dye-surfactant complex which may then be detected in the solvent.

As set out above, the disclosed method contemplates the use of a cationic dye which is capable of complexing with an anionic surfactant from the sample to form a detectable dye-surfactant complex that is preferentially soluble in a solvent which is substantially immiscible with the sample.

The cationic dyes useful in accordance with the disclosed method may include any positively charged (cationic) dyes which are able to complex with an anionic surfactant to produce a detectable dye-surfactant complex that is preferentially soluble in a solvent which is substantially immiscible with the sample.

In further embodiments, the cationic dye is also a base such that upon addition to a sample (at approximately neutral pH) the dye causes an organic acid surfactant in the sample to form its anionic conjugate base, and thus become suitable for detection using the methods of the present invention.

A range of suitable dyes may be used for the detection of anionic surfactants including, for example, ethyl violet, methylene blue, acridine orange, brilliant green and malachite green, amongst others.

However, it has been determined that cationic dyes of the triarylmethane class are particularly suitable for use in accordance with the disclosed method.

In some embodiments of the present invention, the cationic dye of the triarylmethane class comprises the structure (I):

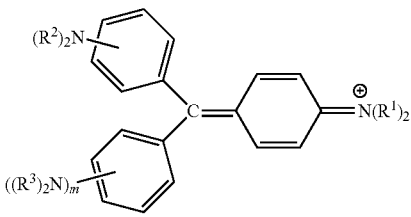

wherein each of $R^1$, $R^2$ and $R^3$ is independently selected from the group consisting of optionally substituted $C_i$-$C\beta$ alkyl; and m is selected from the group consisting of 0 and 1.

In one particular embodiment, m is 1 and each of $R^1$, $R^2$ and $R^3$ are ethyl groups. A dye having this structure is referred to herein as ethyl violet.

In specific embodiments of disclosed method, the cationic dye used is "ethyl violet or a derivative thereof". "Derivatives" of ethyl violet, as referred to herein, include other cationic dyes comprising the structure (I) and/or other cationic dyes of the triarylmethane class.

As set out above, the method also contemplates the use of a solvent which is substantially immiscible with the sample into which the dye-surfactant complex is preferentially soluble.

As referred to herein the term "preferentially soluble" should be understood to refer to an increased level or rate of solubility of the dye-surfactant complex in the solvent than in the sample. Preferential solubility also encompasses the partitioning of the dye-surfactant complex into the solvent from the sample.

Without limiting the present disclosure to any particular mode of action, in the disclosed method, the hydrophilic (anionic) head of the anionic surfactant in a sample complexes with the cationic dye to form a dye-surfactant complex. This complex then preferentially dissolves or partitions into the solvent phase, wherein it can be detected using one of several detection methods (described later).

Solvents which are substantially immiscible with the sample generally include organic solvents such as ethyl acetate, chloroform, toluene, dichloromethane and the like.

As set out earlier, the standard MBAS assay for the detection of anionic surfactants uses chloroform as a solvent. Chloroform exposure is known to cause liver and kidney toxicity. In addition, chloroform is a known teratogen and suspected carcinogen. In light of the toxicity of chloroform, it is not a desirable solvent. In addition, the use of chloroform also makes the MBAS assay particularly poorly suited for use in the field, wherein the risk of user and/or environmental chloroform contamination and/or toxicity is increased.

However, it has been determined that the solvent ethyl acetate is particularly suitable. Ethyl acetate has lower toxicity and carcinogenicity relative to chloroform as used in the standard MBAS assay.

In some embodiments of the disclosed method, the cationic dye comprises ethyl violet or a derivative thereof and the solvent comprises ethyl acetate. Methods which utilise the combination of ethyl violet or a derivative thereof as a dye and ethyl acetate as a solvent are referred to herein as Ethyl Violet Ethyl Acetate Active Substances (EVEA-AS) methods or assays. One specific embodiment of an EVEA-AS assay is set out in the examples.

It has been determined that the EVEA-AS assay provides increased sensitivity and resolution for the detection and/or quantification of anionic surfactants over standard anionic surfactant detection methods such as the MBAS assay.

As referred to herein, the improved sensitivity of the EVEA-AS assay, particularly when compared to the MBAS assay, should be understood to include reference to the lower detection limit of the EVEA-AS assay. As set out in the examples, the improved sensitivity of the EVEA-AS assay over the MBAS assay is particularly apparent when an anionic surfactant is detected and/or quantified by visual detection of a coloured dye-surfactant complex in the solvent phase of the assay (see later for a discussion of detection methods).

In addition to improved sensitivity relative to the MBAS assay, the EVEA-AS assay also exhibits improved resolution relative to the MBAS assay. As referred to herein, the term "resolution" should be understood as the ratio of the amount of detectable dye-surfactant complex generated in the assay relative to the amount of anionic surfactant in the sample. For example, high resolution should be understood to refer to a relatively large amount of detectable dye-surfactant complex generated for a given amount of anionic surfactant in the sample. Conversely, low resolution should be understood as a relatively small amount of detectable dye-surfactant complex generated for the same amount of anionic surfactant in the sample.

In light of the foregoing, it will be appreciated that the resolution of an assay may be represented by the slope of a graphical calibration line for the assay which relates the amount of detectable dye-surfactant complex in the solvent phase (on the y-axis) with increasing known amounts of anionic surfactant in a sample (on the x-axis). In this case, increased resolution of an assay is represented by an increased slope of the calibration line.

Due to the increased response of a high resolution assay to an anionic surfactant in a sample, it would also be appreciated that increased resolution of an assay would also allow discrimination between smaller anionic surfactant concentration differences between different samples.

On the basis of the above definition, the examples demonstrate that the EVEA-AS assay has increased resolution compared to both the MBAS assay and a range of other dye-solvent combination assays.

Thus, in further embodiments, the disclosed method provides a method for the detection of an anionic surfactant in a sample, wherein the method comprises a relative resolution, as measured by the slope of a calibration line for an LAS standard, at a concentration between 0.5 mg/L and 5 mg/L, of at least 0.32, at least 0.35, at least 0.40, at least 0.45 or at least 0.5.

In yet further embodiments, the disclosed method of the present invention provides a method for the detection of an anionic surfactant in a sample, wherein the method comprises a relative resolution, as measured by the slope of a calibration line for an SDS standard, at a concentration between 0.5 mg/L and 5 mg/L, of at least 0.35, at least 0.40, at least 0.45 or at least 0.50.

In yet further embodiments, the disclosed method of the present invention provides a method for the detection of an anionic surfactant in a sample, wherein the method comprises a relative resolution, as measured by the slope of a calibration line for a PFOS standard, at a concentration between 0.25 mg/L and 1 mg/L, of at least 1.8, at least 2.0, at least 2.2 or at least 2.4.

Furthermore, the EVEA-AS assay is also particularly suitable for a field-based assay for anionic surfactants. This is in part due to the use of the relatively safe solvent ethyl acetate, which enables the performance of the assay outside of controlled laboratory conditions and also potentially by relatively unskilled personnel. Furthermore, the increased sensitivity and resolution of the assay is also particularly well suited to visual assessment of the results of the assay (see later), and thus is well suited for detection and/or quantification of anionic surfactants in the field without the use of bulky equipment such as a spectrophotometer.

In the disclosed method, an anionic surfactant in the sample complexes with the cationic dye to form a "detectable dye-surfactant complex" that is preferentially soluble in the solvent which is substantially immiscible with the sample.

As used herein, the term "detectable dye-surfactant complex" refers to any complex formed between the cationic dye and anionic surfactant that is subsequently detectable in the solvent phase of the assay. The dye-surfactant complex may be detected and/or quantified using any suitable method.

In some embodiments of the method, the dye-surfactant complex is detected in the solvent phase using an optical detection method. As referred to herein, "optical detection methods" include any methods which detect the dye-surfactant complex on the basis of absorption, reflection or refraction of light at one or more wavelengths.

In some embodiments, the dye-surfactant complex formed by the anionic surfactant and the cationic dye may be coloured. In these embodiments, the dye-surfactant complex may be detected in the solvent phase by detection and/or quantification of a colour change in the solvent phase of the assay.

In one embodiment, a colour change in the solvent phase of the assay may be detected and/or quantified by visual inspection. In order to quantify the amount of dye-surfactant complex in the solvent phase, the visual inspection may comprise comparison of the colour of the solvent with one or more visual reference colours. The "visual reference colours" for use in accordance with the assay may be predetermined colours comprising the colour of the solvent phase when the assay is used with a known concentration of anionic surfactant in a sample. Quantification of the anionic surfactant in an unknown sample is then performed by matching the colour of the solvent phase from the assay of the unknown sample with the closest reference colour and then reading the known concentration associated with the closest reference colour.

In alternative embodiments, the optical detection method comprises spectrophotometry. Spectrophotometry methods are well known in the art and will not be described herein in detail. Typically, spectrophotometry is performed at a wavelength that is the same as, or close to, the peak absorbance of the product to be detected. As such, spectrophotometric detection of the product may occur in any suitable spectrum of light, including, for example the visible, ultraviolet or infrared spectra. In the case of ethyl violet, the peak absorbance of this dye is at a wavelength of 596 ran. Thus, spectrophotometric detection of an ethyl violet-containing complex is typically performed at about 596 ran. In the case of products with unknown absorbance peaks, these may be determined experimentally by obtaining an absorbance spectrum of the product across a range of wavelengths.

In some embodiments, the method further comprises a concentration step to increase the concentration of one or more anionic surfactants in the sample prior to contacting the sample with the cationic dye and/or solvent.

The concentration step may include any concentration step that increases the concentration of an anionic surfactant in a sample. Exemplary concentration steps include for example, solid phase extractions (SPE), solvent evaporation, solvent sublimation (eg. freeze-drying), preparative chromatography (eg. preparative TLC, preparative HPLC or preparative GC) and the like.

The concentration step may be used, for example, to increase the concentration of an anionic surfactant in an environmental sample to within the detection range of an assay according to the present invention. As will be appreciated, if a concentration step is used in a quantitative assay, the concentration result obtained from the assay must take into account the concentration factor of the concentration step.

In some embodiments, the concentration step may comprise a solid phase extraction (SPE). A range of suitable SPE methods for the concentration of anionic surfactants from a sample would be readily ascertained by a person skilled in the art. In this regard, reference is made to Solid-Phase Extraction: Principles, Techniques, and Applications, Simpson, N. K. (Ed.), CRC Press, 2000. Reference is also made to example 3 where an exemplary SPE method is disclosed.

As would be appreciated, for samples having high surfactant concentrations, a dilution step may also be used to bring the concentration of the assayed sample into the detection range of the method.

In a second aspect, the present invention provides a kit for detecting and/or quantifying an anionic surfactant in a sample, the kit comprising:

a cationic dye, wherein the cationic dye is capable of complexing with an anionic surfactant from the sample to form a detectable dye-surfactant complex that is preferentially soluble in a solvent which is substantially immiscible with the sample; and instructions for performing the method according to the first aspect of the invention.

The cationic dye used in the kit may comprise a cationic dye as hereinbefore described with regard to the disclosed method. As such, in some embodiments, the cationic dye comprises ethyl violet or a derivative thereof In some embodiments, the kit may further comprise a solvent which is substantially immiscible with the sample, as hereinbefore described with regard to the disclosed method. As such, in some embodiments, the solvent comprises ethyl acetate.

In further embodiments, the kit of the present invention may also further comprise a reaction vessel for contacting the sample with the cationic dye and/or solvent.

The reaction vessel included in the kit may be any suitable reaction vessel for the assay of the present invention such as a test tube, screw cap tube or vessel, flask or the like.

In yet further embodiments, the kit may also further comprise one or more reference objects, each comprising one or more reference colours, for detecting and/or quantifying the dye-surfactant complex in the solvent.

The one or more reference colours correspond to colours of the solvent phase when the assay is performed on a sample having a known concentration of an anionic surfactant. A range of suitable reference colours, corresponding to a range of known anionic surfactant concentrations in a sample, may be included in a kit. In this way, when the assay is performed on a sample having an unknown concentration of anionic surfactant, the colour of the solvent phase after the assay is performed may be compared with one or more of the reference colours to provide an estimation of the concentration of the anionic surfactant in the sample having the unknown concentration.

The one or more "reference objects" comprising the one or more reference colours may comprise any suitable coloured object such as a colour chart. Alternatively, one or more reference colours may be incorporated into one or more of the other components of the kit, such as being printed on a reaction vessel or incorporated into the packaging of the kit.

The kits of the present invention may be used for detecting any suitable anionic surfactant, as set out above. However, in some specific embodiments, the kits of the present invention are suitable for detecting an anionic surfactant constituent of an aqueous film forming foam and/or a fluorinated anionic surfactant.

The present invention is further described by the following non-limiting examples.

Example 1

Ethyl Violet Ethyl Acetate Active Substances (EVEA-AS) Assay

A method for the detection of anionic surfactants according to one embodiment of the present invention is presented. This method uses the combination of the dye ethyl violet with ethyl acetate as a solvent, and thus is an embodiment of an EVEA-AS method as previously described.

As set out below, when compared to the standard MBAS method, this method is more sensitive to lower concentrations of anionic surfactants and can be used in the field without exposure to the toxic solvent chloroform.

Materials and Methods

All glassware for use in the method was cleaned with acetone 3× and methanol 3×. Glassware was not cleaned with detergent.

An ethyl violet solution comprising 0.0064 g ethyl violet in 200 mL Milli-Q water (32 mg per L) was prepared.

To perform the assay, 1 mL of ethyl violet solution (described above) was added to 8 mL of a water sample. Subsequently, 3 mL of ethyl acetate was added to the water sample. The sample-dye-solvent mixture was then shaken vigorously, before being allowed to stabilize and form two phases.

The presence of a coloured dye-surfactant complex was then assessed in the ethyl acetate solvent phase. A non-acidified calibration curve (LAS) or non-acidic standard coloration chart was used to estimate an anionic surfactant concentration in the sample.

In an alternative embodiment, a spectrophotometer was used to detect the presence of the coloured dye-surfactant complex in the solvent phase. In this embodiment, the absorbance of the solvent phase was measured at 595 ran.

Data and Results

Figure 2:
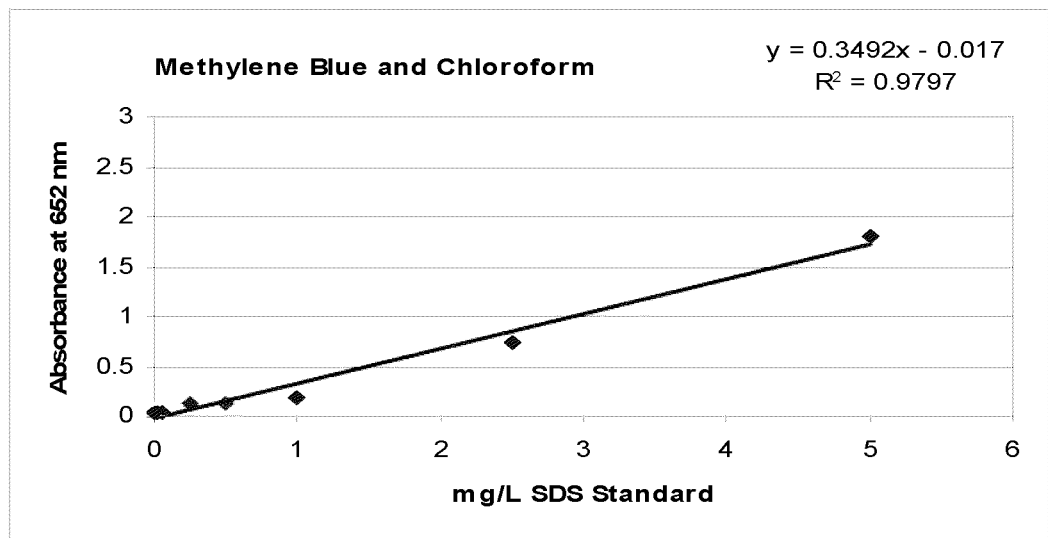
FIG. 2 shows a comparison of the MBAS assay with the EVEA-AS assay using SDS as a calibration standard. Panel A shows absorbance in the solvent phase after using the MBAS assay with varying concentrations of SDS in a sample. Panel B shows absorbance in the solvent phase after using the EVEA-AS assay with varying concentrations of SDS in a sample.
Figure 2:
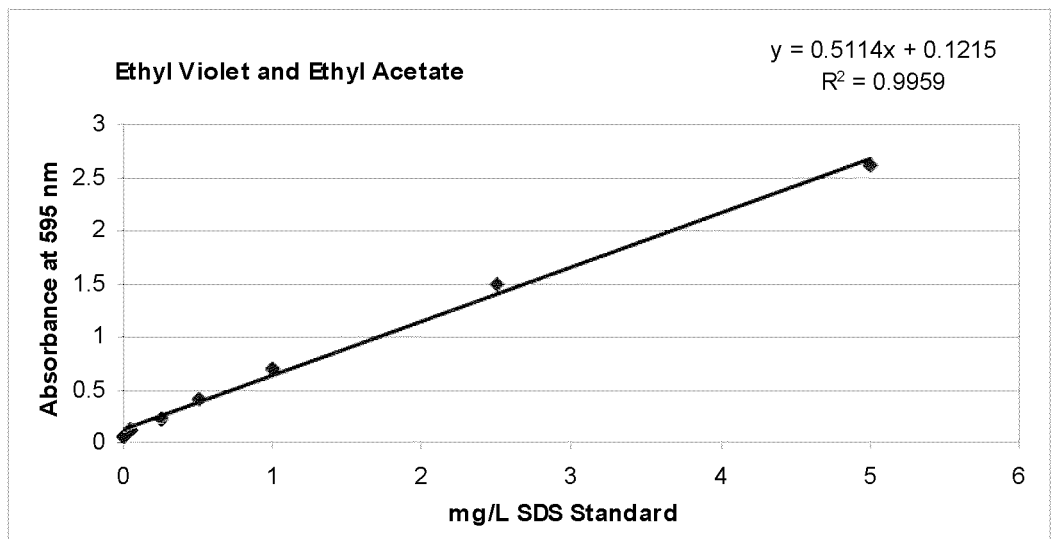
Figure 3:
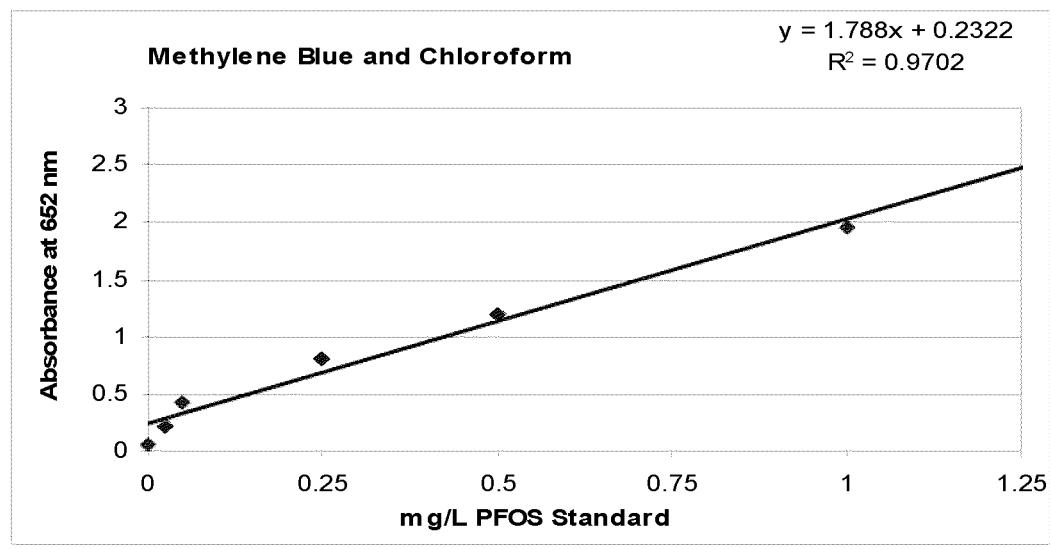
FIG. 3 shows a comparison of the MBAS assay with the EVEA-AS assay using PFOS as a calibration standard. Panel A shows absorbance in the solvent phase after using the MBAS assay with varying concentrations of PFOS in a sample. Panel B shows absorbance in the solvent phase after using the EVEA-AS assay with varying concentrations of PFOS in a sample.
Figure 3:
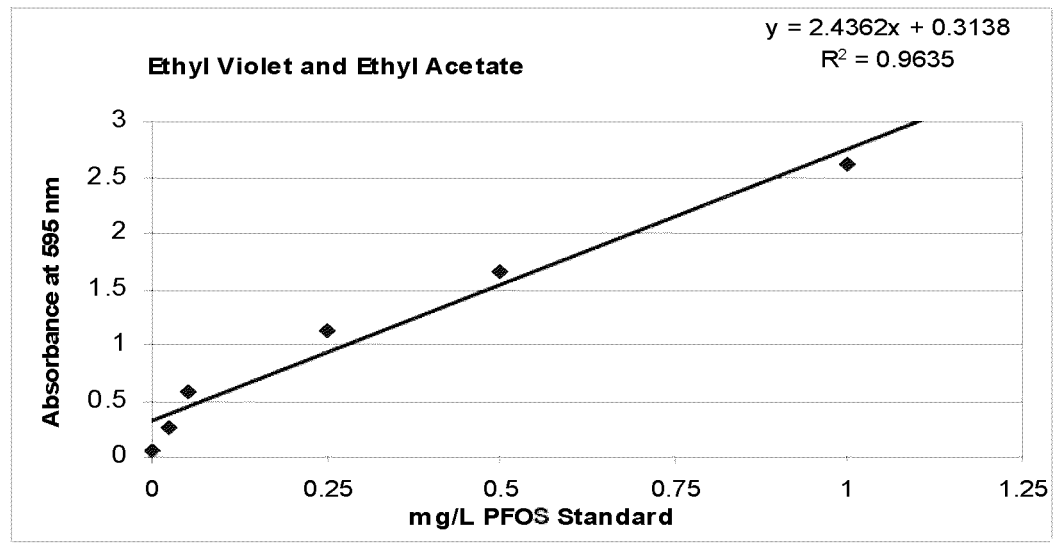

FIGS. 1, 2 and 3 show the comparison of the MBAS assay with the EVEA-AS assay using three calibration standards of anionic surfactants.

As shown in FIGS. 1, 2 and 3, the greater slope of the calibration line for the EVEA-AS assay with each anionic surfactant standard indicated that the EVEA-AS method yields a greater resolution than the MBAS assay. That is, the EVEA-AS method yields a greater increase in absorbance and subsequent color change in the solvent phase for equivalent concentrations of each standard than the MBAS assay.

The detection limit of EVEA-AS using a spectrophotometric plate reader at 595 ran is 0.02 mg/L LAS versus 0.025 mg/L LAS with MBAS at 652 ran.

Visual limits of detection, ie. dye-surfactant complex detection and/or quantification by visual comparison with a colour reference, of the EVEA-AS method are 0.075 mg/L LAS versus 0.175 mg/L LAS with the MBAS assay.

The calibration range suggested for spectrophotometer-based detection methods of the EVEA-AS extraction method is from 0.02 mg/L to 3.25 mg/L. The MBAS assay detection limit is published at 0.025 mg/L.

Example 2

Comparison of the EVEA-AS assay with dye/solvent combinations

Figure 4:
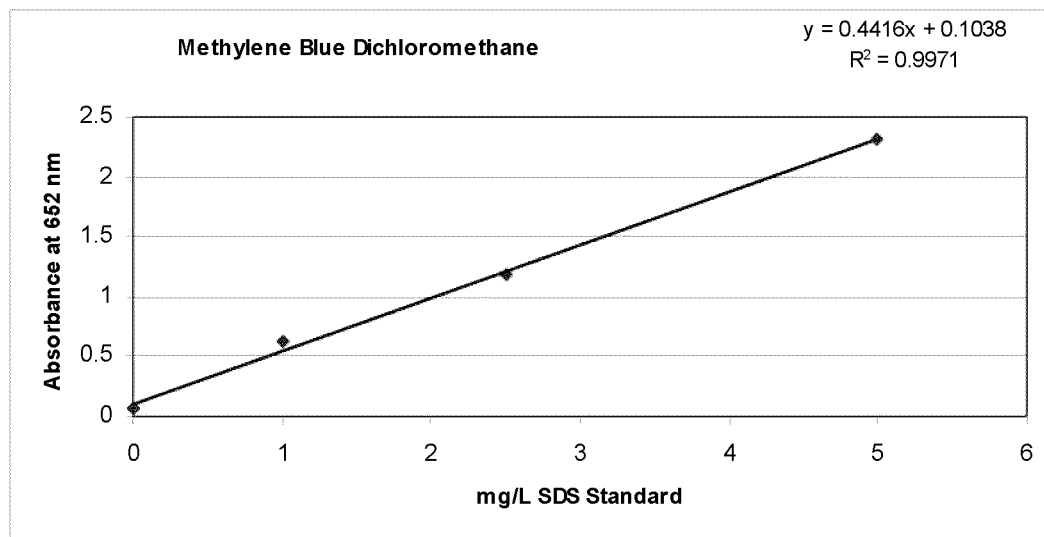
FIG. 4 shows a comparison of anionic surfactant detection methods using various dye/solvent combinations. In each case, the anionic surfactant being detected was various concentrations of SDS. Panel A shows the results for a methylene blue/dichloromethane based method; panel B shows the results for an acridine orange/toluene based method; panel C shows the results for a brilliant green/toluene based method; panel D shows the results for a malachite green/ethyl acetate based method.
Figure 4:
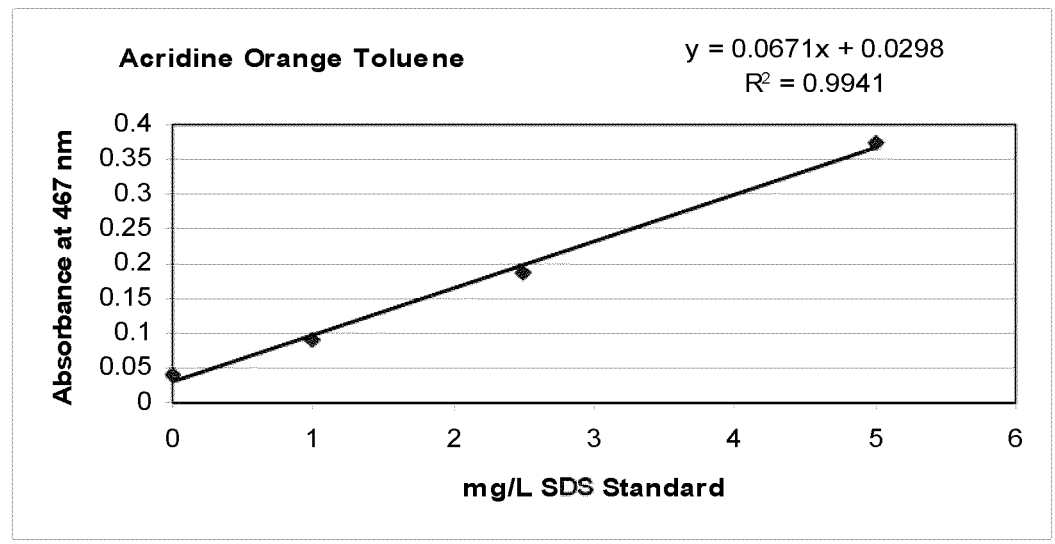
Figure 4:
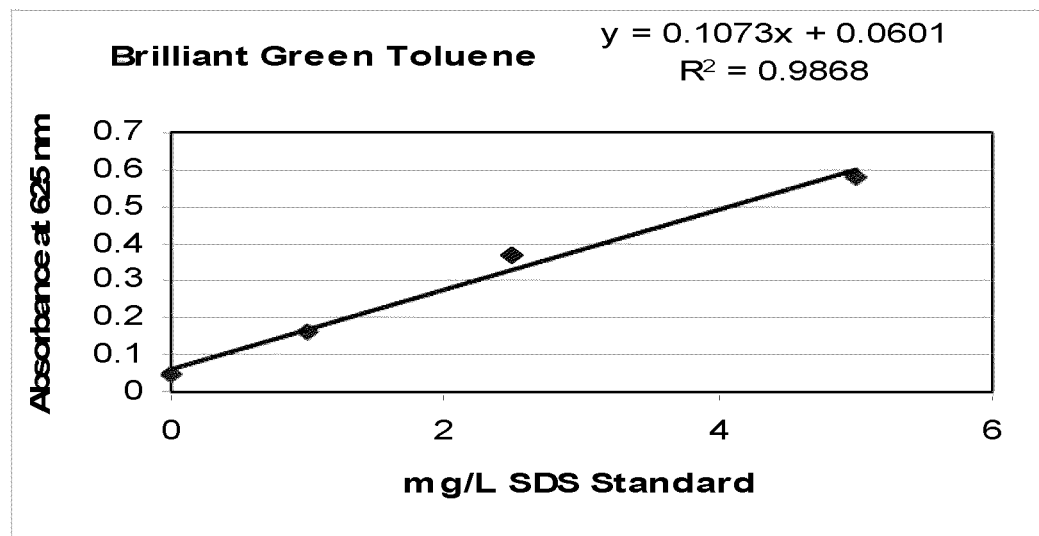
Figure 4:
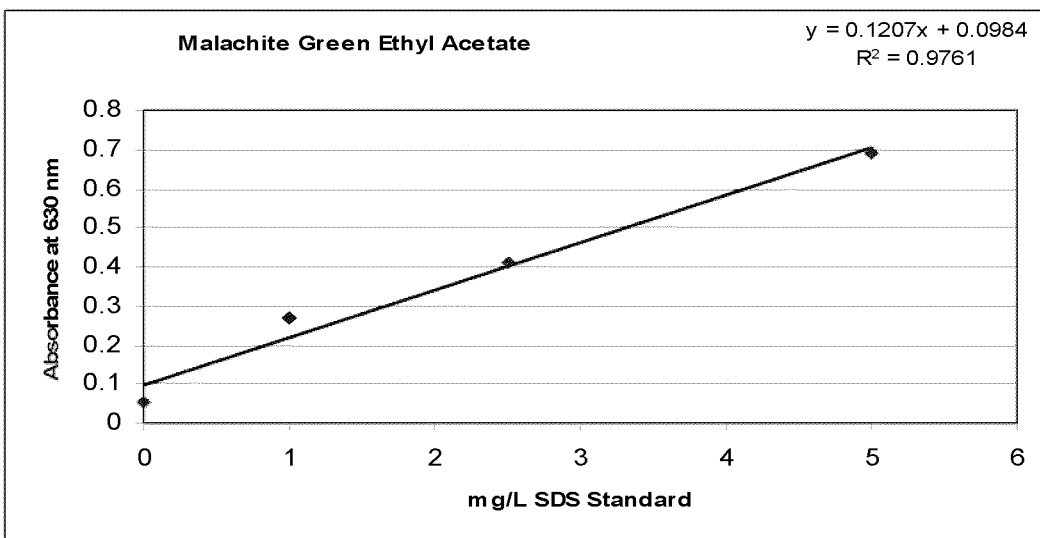

FIG. 4 shows a comparison of the results obtained using a variety of alternate dye/solvent combinations in assays for the detection of an anionic surfactant. The components used in these assays and the results are presented in Table 2 below.

Each of the dyes for the comparative assays, other than acridine orange, were prepared in the same way and at the same concentration as described for ethyl violet in example 1. Acridine orange was prepared to a concentration of 0.005M in MilliQ water.

In each case, the assay was performed by adding 1 mL of the appropriate dye solution to an 8 mL water sample containing known concentrations of the anionic surfactant SDS.

Subsequently, 3 mL of the appropriate solvent was added to the water sample. The sample-dye-solvent mixture was then shaken vigorously, before being allowed to stabilize and form two phases.

The formation of a coloured dye-surfactant complex in the solvent phase was then determined using spectrophotometry.

TABLE 2

Comparison of anionic surfactant detection methods using different dye/solvent combinations using an SDS standard.

| Dye | Solvent | Relative Resolution[1] |
|---|---|---|
| Methylene blue | Dichloromethane | 0.4416 |
| Acridine orange | Toluene | 0.0298 |

TABLE 2-continued

Comparison of anionic surfactant detection methods using different dye/solvent combinations using an SDS standard.

| Dye | Solvent | Relative Resolution[1] |
|---|---|---|
| Brilliant Green | Toluene | 0.0601 |
| Malachite Green | Ethyl Acetate | 0.0984 |
| Methylene Blue | Chloroform | 0.3492[3] |
| Ethyl Violet | Ethyl Acetate | 0.5114[3] |

[1]Relative resolution represented by the slope of the calibration line using SDS.
[2]Data taken from example 1.

In addition, the EVEA-AS assay had increased resolution (as measured by the slope of the calibration line) for the anionic surfactant SDS than each of the other dye/solvent combinations tested.

Example 3

Solid Phase Extraction

For some samples, such as some environmental samples, it may be desirable to concentrate an anionic surfactant in the sample prior to detecting an anionic surfactant. For example, it may be desirable to first concentrate an anionic surfactant in a sample when the level of surfactant in the original sample is low, and potentially lower than the detection limit of the assay.

When concentration of a sample is required, an anionic surfactant may be concentrated in the sample using Solid Phase Extraction (SPE). An exemplary SPE protocol that is suitable for use with the disclosed method is described below.

A water sample was acidified by adding 1 drop 1 M Hydrochloric acid to every 8 mL of water sample, or 3-4 drops 1 M nitric acid (HNO3) to every 8 mL of water sample.

0.5 grams of silica SPE medium was used after activation of the silica at 200° C. for 4-6 hours. The SPE medium was then charged with ~5 mL Acetone. After charging, the SPE medium was then rinsed 2-3× with ~5 mL MQ water.

After rinsing, the sample was loaded onto the medium under minimal vacuum at a rate of ~5-6 mL/minute. Anionic surfactant in the sample bound to the SPE medium.

Anionic surfactant bound to the SPE medium was then eluted from the SPE medium in 2 mL of Acetone at a rate of ~1-2 mL/minute.

The eluate from the SPE medium (containing the anionic surfactant) was then mixed with 8 mL MQ water, 3 mL ethyl acetate and 1 mL ethyl violet solution as described above for the EVEA-AS assay. A calibration curve (LAS) with 2 mL acetone coloration chart was then used to estimate anionic surfactant concentration in the sample (taking into account the concentration of the sample).

On average, the recovery of a mid-level LAS standard (approximately 0.375 mg/L) used in the MBAS assay in the SPE method to concentrate samples was 100%, see Table 3 below:

TABLE 3

Absorbance and recovery of 0.5 gram Silica SPE replicates compared to direct extraction of LAS standard.

| Sample | Absorbance | Absorbance Average | Absorbance SD | Recovery compared to direct extraction |
|---|---|---|---|---|
| SPE replicate 1 | 0.205 | 0.212 | 0.023 | 100% |
| SPE replicate 2 | 0.188 | | | |
| SPE replicate 3 | 0.249 | | | |
| SPE replicate 4 | 0.214 | | | |
| SPE replicate 5 | 0.205 | | | |
| Direct extraction | 0.217 | 0.212 | 0.006 | |
| Direct extraction | 0.205 | | | |
| Direct extraction | 0.216 | | | |

The use of the 0.5 gram activated silica SPE also produces >85% recoveries for both SDS and PFOS.

Figure 5:
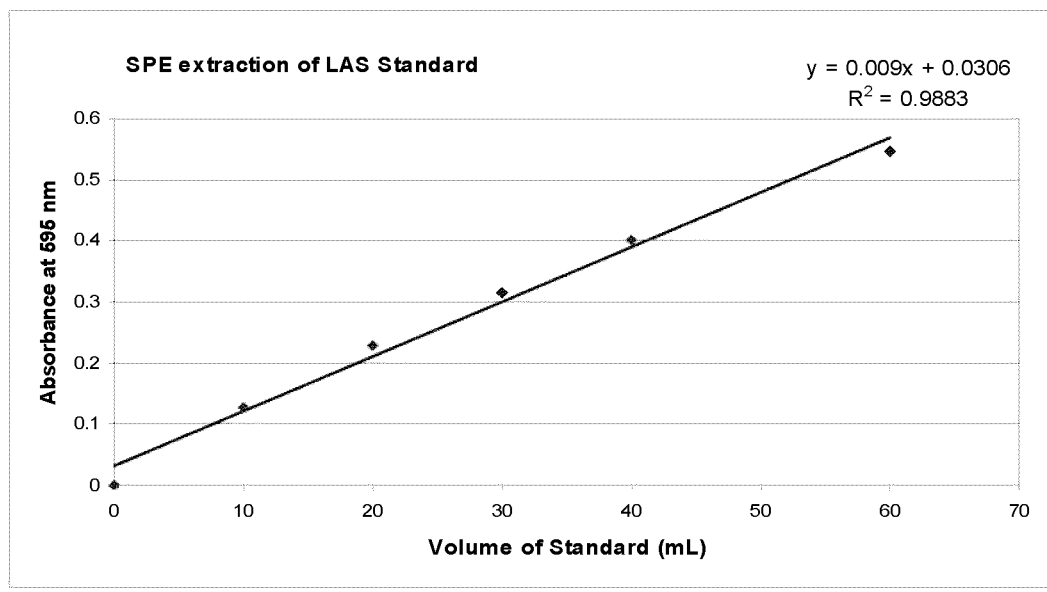
FIG. 5 shows absorbance of increasing volumes (mL) of LAS standard after concentration onto 0.5 gram silica SPE columns.

This method was tested with increasing volume of standards of LAS onto the SPE cartridge (FIG. 5) to validate the test for higher volume of samples without loss of compounds of interest.

These results indicate that SPE may be used to concentrates anionic surfactant in dilute samples to within the linear range of the EVEA-AS method.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

Also, it must be noted that, as used herein, the singular forms "a", "an" and "the" include plural aspects unless the context already dictates otherwise. Thus, for example, reference to "an anionic surfactant" includes a type of surfactant as well as two or more surfactant types; and so forth.

What is claimed is:

1. A method for detecting and/or quantifying an anionic surfactant in a sample, the method comprising:
    contacting a cationic dye with either a sample and a solvent or an extract of the sample in the solvent such that an anionic surfactant in the sample or extract complexes with the cationic dye to form a detectable dye-surfactant complex that is preferentially soluble in the solvent, the cationic dye comprising at least one of ethyl violet and a derivative thereof and the solvent comprising ethyl acetate and being substantially immiscible with the sample; and
    detecting and/or quantifying the dye-surfactant complex in the solvent, wherein the presence of the dye-surfactant complex in the solvent indicates the presence of an anionic surfactant in the sample.

2. The method of claim 1, wherein the sample comprises a water sample.

3. The method of claim 1, wherein the sample comprises a soil sample.

4. The method of claim 1, wherein the method further comprises a concentration step to increase the concentration of one or more anionic surfactants in the sample prior to contacting the sample with the cationic dye and/or solvent.

5. The method of claim 4, wherein the concentration step comprises solid phase extraction.

6. The method of claim 1, wherein the dye-surfactant complex is detected and/or quantified in the solvent using an optical detection method.

7. The method of claim 6, wherein the optical detection method comprises visual inspection of the solvent.

8. The method of claim 7, wherein the visual inspection comprises comparison of the colour of the solvent with one or more visual reference colours.

9. The method of claim 7, wherein optical detection method comprises spectrophotometry.

10. The method of claim 1, wherein the anionic surfactant comprises an anionic surfactant constituent of an aqueous film forming foam.

11. The method of claim 1, wherein the anionic surfactant comprises a fluorinated anionic surfactant.

12. A kit for detecting and/or quantifying an anionic surfactant in a sample, the kit comprising:
   a cationic dye, wherein the cationic dye is capable of complexing with an anionic surfactant from the sample to form a detectable dye-surfactant complex that is preferentially soluble in a solvent which is substantially immiscible with the sample, the cationic dye comprising at least one of ethyl violet and a derivative thereof, and the solvent comprising ethyl acetate; and
   instructions for performing the method of claim 1.

13. The kit of claim 12, further comprising a solvent which is substantially immiscible with the sample.

14. The kit of claim 12, further comprising a reaction vessel for contacting the sample with the cationic dye and/or solvent.

15. The kit of claim 12, further comprising one or more reference objects, each comprising one or more reference colours, for detecting and/or quantifying the dye-surfactant complex in the solvent.

16. The method according to claim 8, wherein the visual detection limit of anionic surfactant in the sample is 0.075 mg/L.

* * * * *

UNITED STATES PATENT AND TRADEMARK OFFICE
CERTIFICATE OF CORRECTION

| | | |
|---|---|---|
| PATENT NO. | : 9,103,797 B2 | Page 1 of 1 |
| APPLICATION NO. | : 13/622425 | |
| DATED | : August 11, 2015 | |
| INVENTOR(S) | : Megharaj Mallavarapu et al. | |

It is certified that error appears in the above-identified patent and that said Letters Patent is hereby corrected as shown below:

On the title page item (30), Foreign Application Priority Data: Delete "Oct. 8, 2008" and replace with -- Oct. 9, 2008 --

Signed and Sealed this
Twenty-second Day of December, 2015

Michelle K. Lee
*Director of the United States Patent and Trademark Office*